United States Patent
Arndt et al.

(10) Patent No.: US 8,221,435 B2
(45) Date of Patent: Jul. 17, 2012

(54) DEVICE COMPRISING A PIN SUPPORT MEMBER AND INSULATION MEANS FOR FIXATION TO A PATIENTS SKULL DURING NEUROLOGICAL DIAGNOSIS, AND A METHOD FOR ASSEMBLING SAID DEVICE

(75) Inventors: Jürgen Arndt, Färentuna (SE); Bo Nilsson, Österskär (SE); Jan-Erik Olsson, Linköping (SE)

(73) Assignee: Elekta AB (Publ), Stockholm (SE)

( * ) Notice: Subject to any disclaimer, the term of this patent is extended or adjusted under 35 U.S.C. 154(b) by 2077 days.

(21) Appl. No.: 10/513,508

(22) PCT Filed: May 6, 2003

(86) PCT No.: PCT/SE03/00723
§ 371 (c)(1),
(2), (4) Date: Dec. 10, 2004

(87) PCT Pub. No.: WO03/094769
PCT Pub. Date: Nov. 20, 2003

(65) Prior Publication Data
US 2005/0131425 A1    Jun. 16, 2005

(30) Foreign Application Priority Data
May 8, 2002   (SE) .................................. 0201399

(51) Int. Cl.
*A61B 19/00*   (2006.01)
(52) U.S. Cl. ........................................ 606/130; 602/17
(58) Field of Classification Search ................. 600/415; 602/36, 37, 17, 74; 606/54, 75, 130, 304, 606/318, 289, 290; 403/6, 7, 9, 336
See application file for complete search history.

(56) References Cited

U.S. PATENT DOCUMENTS

| | | | | |
|---|---|---|---|---|
| 1,398,842 A | * | 11/1921 | Cruse | 606/130 |
| 3,508,552 A | * | 4/1970 | Hainault | 606/130 |
| 3,835,861 A | * | 9/1974 | Kees et al. | 5/637 |
| 4,386,602 A | * | 6/1983 | Sheldon et al. | 600/102 |
| 4,397,307 A | | 8/1983 | Keller | |
| 4,612,930 A | * | 9/1986 | Bremer | 606/130 |
| 5,042,462 A | | 8/1991 | Bremer | |
| 5,156,588 A | * | 10/1992 | Marcune et al. | 602/17 |
| 5,197,965 A | * | 3/1993 | Cherry et al. | 606/54 |

(Continued)

OTHER PUBLICATIONS http://www.engineeringtoolbox.com/resistivity-conductivity-d_418.html; "Resistivity, Conductivity and Temperature Coefficients for some common materials".*

(Continued)

*Primary Examiner* — Ryan Severson
*Assistant Examiner* — David Eastwood
(74) *Attorney, Agent, or Firm* — Birch, Stewart, Kolasch & Birch, LLP

(57) ABSTRACT

The present invention relates to a device for fixation to a patient during neurological diagnosis, therapy or surgery, in particular during MRI diagnosis. The device comprises at least one fixation pin being made of a non-magnetic, electrically conductive material for fixation to a patient, and at least one pin support member for supporting said fixation pin. An insulation means is arranged so as to restrict the electrical coupling between said pin support member and fixation pin. Said insulation means is sleeve shaped and arranged to at least partly surround said fixation pin. The invention also relates to an insulation means, a pin support member and to a method for assembling a fixation device.

15 Claims, 3 Drawing Sheets

U.S. PATENT DOCUMENTS

| | | | |
|---|---|---|---|
| 5,380,336 A * | 1/1995 | Misko et al. | 606/130 |
| 5,643,268 A | 7/1997 | Vilsmeier et al. | |
| 5,961,528 A | 10/1999 | Birk et al. | |
| 6,045,553 A | 4/2000 | Iversen et al. | |
| 2001/0029379 A1 * | 10/2001 | Grotehuis et al. | 606/130 |
| 2002/0007188 A1 * | 1/2002 | Arambula et al. | 606/130 |
| 2002/0042619 A1 * | 4/2002 | Dominguez et al. | 606/130 |
| 2002/0151907 A1 * | 10/2002 | Day et al. | 606/130 |

OTHER PUBLICATIONS

Excerpt from an internet web page Apr. 19, 2002: www.erads.com/mrsafety.htm with title "Module #5: MRI Safety" by Judith Behrens, RT, MR Applications Specialist, Siemens Medical Systems, Greensboro, NC.

* cited by examiner

DEVICE COMPRISING A PIN SUPPORT MEMBER AND INSULATION MEANS FOR FIXATION TO A PATIENTS SKULL DURING NEUROLOGICAL DIAGNOSIS, AND A METHOD FOR ASSEMBLING SAID DEVICE

FIELD OF THE INVENTION

The present invention relates to a device for fixation to a patient during neurological diagnosis, therapy or surgery, in particular during MRI diagnosis. The device comprises at least one fixation pin being made of a non-magnetic, electrically conductive material for fixation to a patient, and at least one pin support member for supporting said fixation pin.

The invention also relates to a pin support member for supporting a pin in a fixation device for fixation to a patient during neurological diagnosis, therapy or surgery, to an insulation means and to a method for assembling a fixation device.

BACKGROUND OF THE INVENTION

During neurological surgery, therapy or diagnosis, it is common practice to work with a reference system being fixed in relation to the head of the patient using some type of fixation device. The reference system is used to determine the location of different areas in the involved part/tissue of the patient.

An example of such a reference system is a so-called stereotactic frame with posts having fixation pins for invasive fixation to the skull of a patient. In use during for example MRI (Magnetic Resonance Imaging) diagnostics, the stereotactic frame is arranged around the head of a patient, and the fixation pins of the posts connected to the frame are screwed to the bone of the skull, thus ensuring a rigid fixation of the reference system.

The frame is then rigidly held in position in relation to a MRI table.

For use in MRI diagnostics, all parts of the stereotactic frame, the posts and pins must be made of non-magnetic material. For the frame and posts, aluminium is often used. For the pins, several different materials have been proposed.

U.S. Pat. No. 5,643,268 (Vilsmeier) discloses fixation pins having a threaded plastic shaft and a separate point of semi-precious stone material. These fixation pins are disposable; used only one and then discarded.

Another type of fixation pins are re-usable fixation pins, that need to be sterilised between each use. Preferably, the pins should be sterilisable in an autoclave, being a practically available sterilisation means in hospitals.

Known re-usable fixation pins are for example made of aluminium with a tip of hard metal. Recently, also fixation pins made of titanium have come into use. The titanium pins have the advantage that they are easier to manufacture than the previously used aluminium—hard metal pins. Titanium pins are also readily sterilisable in common autoclave means. Further, titanium have advantageous strength properties. This is useful, for example in that a titanium pin may be made having an internal structure such as a hexagonal blind bore for seating of a screw driver when adjusting the position of the pin. Internal structures are preferred over external structures, such as external hexagonal seats, since extending structures take up more space.

For the frame posts, aluminium has, as mentioned above, often been used. Also plastic posts are available. However, some of the plastic posts have the disadvantage that they are somewhat more resilient than aluminium, thus risking inadvertent bending of the posts, resulting possibly in inaccurate references being used in surgery or diagnostics. Also, plastic posts have limited durability in that they become weakened by the sterilisation procedures and therefore only can withstand a limited number of sterilisations.

One example of plastic posts is found in U.S. Pat. No. 4,612,930 (Bremer) disclosing posts being made of boron fibre or graphite fibre reinforced plastic.

In view of the above, it is appreciated that many different combinations of known posts and pins may be made, after the choice of the user. However, when using metal posts together with metal pins during MRI diagnostics, it has been found that a volume around the pins may be subject to heating. This effect has been found to be particularly pronounced when using metal posts in combination with titanium pins. Sometimes the heating effect becomes considerable, so that a patient may be affected by the increased temperature.

U.S. Pat. No. 5,961,528 (Birk et al) describes a problem related to a temperature change during MRI diagnosis. A skull pin is suggested which includes a metallic tip section being attached to a rigid, non-metallic insulator, preferably ceramic. The proposed skull pin includes a contact tip, an insulator attached to the tip and extending outwardly therefrom, and a driving portion coupled to the insulator for attachment with the cervical fixation device. Thus, although U.S. Pat. No. 5,961,528 recognises a heating problem, the solution consists of a pin comprising several details of different materials.

Therefore, it is an object of the present invention to provide a fixation device, for which said heating of the pins during MRI diagnostics is diminished in relation to previously known devices, and which enables use of metal posts in combination with conventional metal pins.

SUMMARY OF THE INVENTION

The above object is achieved by a device according to the introduction, in which an insulation means is arranged so as to restrict the electrical coupling between said pin support member and fixation pin. The insulation means is sleeve shaped and arranged to at least partly surround the fixation pin.

It has been found that the provision of an insulation means restricting the electrical coupling between the pin support member and the fixation pin reduces the heating of a volume around said pin during MRI diagnosis.

The heating effect is believed to have its origin in oscillating electromagnetic fields which operate in the lower megahertz range and are used in MRI systems to generate a signal which is measured during each scan. Such oscillating electromagnetic fields are known as radio frequency fields (RF). In a radio frequency field, metal parts may act as antennae whereby the RF field is concentrated. Under certain circumstances, the concentration of the RF field may cause heat to be induced in adjacent materials.

When using a prior art stereotactic frame having metal posts and fixation pins for MRI diagnostics, the RF properties of the combined frame—patient system is such that heat may be induced in the system. The induced heat is primarily concentrated to the volume around the tips of the fixation pins.

The insulation means that is provided according to the invention is believed to act so as to alter the RF properties of the combined frame—patient system, which in turn reduces the heating.

In experiences made by the inventors, using aluminium pin support members in combination with aluminium or titanium pins, the heating effect was found to be more severe when using titanium pins than when using aluminium pins. Accordingly, the advantages of the invention is believed to be especially useful in combination with titanium pins. A particular advantage with the invention is that it enables use of conventional metal pins, that is pins being made entirely out of a metal such as titanium.

The sleeve shape of the insulation means is advantageous in that it enables easy access to the distal portions of the fixation pins for adjustment thereof. If the fixation pin is surrounded by the insulation means such that its distal portion is situated inside the sleeve, the distal portion is nevertheless accessible through the sleeve opening. More advantageous is however to have the fixation pin extending through the insulation means, thus providing easy access to the distal portion of the fixation pin.

An additional advantage with the device according to the invention is that the insulation means prevents the generation of for the patient disturbing noise when the pins are adjusted in the pin support members. In prior art devices such noise is sometimes caused by the friction between pins and pin support members as the positions of the pins are adjusted.

Advantageously, the insulation means is made of a material having an electrical resistivity being greater than the resistivity of any one of said pin support member and said fixation pin, whereby the electrical coupling between the pin support member and the fixation pin is restricted. The insulation means may be made of a material having an electrical resistivity greater than $10^5$ Ωm, preferably greater than $10^8$ Ωm, most preferred greater than $10^{12}$ Ωm.

Preferably, the insulation means is arranged so as to restrict the electrical coupling between the pin support member and the fixation pin to such an extent that the pin support member is electrically insulated from the fixation pin.

The fixation pins may advantageously have a distal portion being provided with an engagement means to be engaged when screwing said fixation pin to or from a fixation position. Such engagement means could for example be a slot or an internal or an external polygonal structure for seating of a screw driver. Advantageously, the insulation means is arranged so as to allow access to said engagement means of the fixation pin. This allows fixation of the device by turning the pins using standard tools for screwing, without being impaired by the presence of the insulation means.

Advantageously, the pin support member is provided with a receiving formation for detachably receiving the insulation means. Thus, the insulation means may form a disposable part, that is discarded after each use, whereas the pin support member and fixation pin may be re-usable, sterilisable parts. This allows for designs and material choices being advantageous out of economical or other aspects.

In a second aspect of the invention, there is provided a pin support member for supporting a pin in a fixation device for fixation of a patient during neurological diagnosis, therapy or surgery, in particular during MRI diagnosis, said pin support member being made of a non-magnetic, electrically conductive material and comprising a support portion for supporting a fixation pin. The above object is achieved by said support portion comprising a through bore in which an insulation means is arranged, which in turn is intended to support said fixation pin.

Alternatively, the object is achieved by said support portion having a receiving formation with a through bore for detachably receiving a sleeve shaped insulation means, which in turn is intended to support said fixation pin.

In a third aspect of the invention there is provided an insulation means for a fixation pin in a fixation device for fixation to a patient during neurological diagnosis, therapy or surgery, in particular during MRI diagnosis, said insulation means being sleeve shaped for at least partly surrounding said fixation pin, and being made of a non-conductive plastic material.

Thus, the insulation means allows access of an engagement means being commonly arranged at the distal end of a fixation pin, for screwing of said pin to or from a fixating position.

In a fourth aspect of the invention there is provided a method for assembling a fixation device for use during neurological diagnosis, therapy or surgery, in particular during MRI diagnosis, comprising the steps of:
  providing said fixation device comprising at least one pin support member for supporting a fixation pin, said pin support member having a receiving formation for receiving an insulation means,
  arranging a sleeve shaped insulation means in said receiving formation, and
  arranging a fixation pin to be supported in said insulation means so that a distal end of said fixation pin is accessible.

Alternatively, the method comprises the steps of:
  providing said fixation device comprising at least one pin support member for supporting a fixation pin, said pin support member having a receiving formation for receiving a sleeve shaped insulation means,
  arranging a fixation pin in a sleeve shaped insulation means, and
  arranging said insulation means with fixation pin in said receiving formation so that a distal end of said fixation pin is accessible.

Further advantages of the invention will appear by way of example in connection with the following description of preferred embodiments, referring to the accompanying drawings in which:

DESCRIPTION OF PREFERRED EMBODIMENTS

Figure 1:
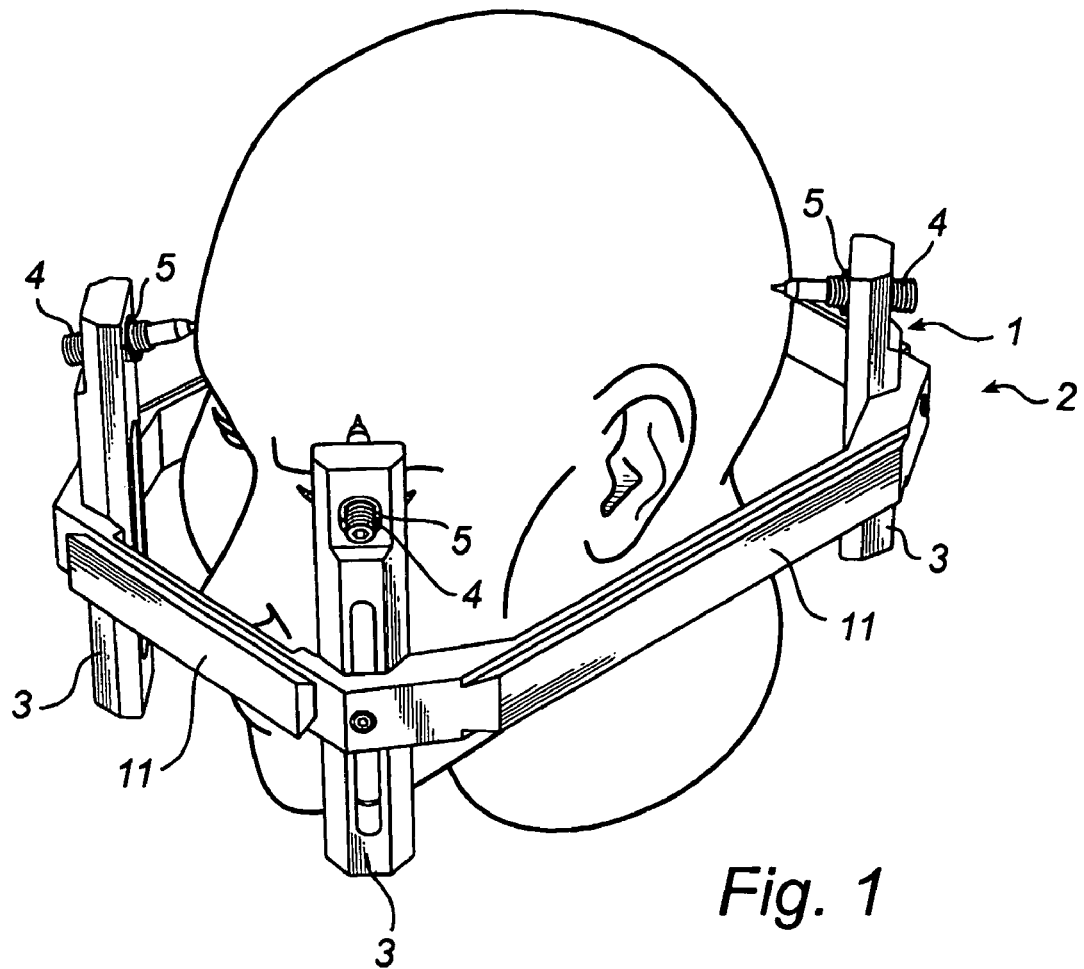
FIG. 1 shows a fixation device according to an embodiment of the invention when in use in a stereotactic frame attached to a patient.

FIG. 1 shows a fixation device 1 according to an embodiment of the invention when in use with a stereotactic frame 2 and fixed to the head of a patient.

The fixation device 1 in this embodiment comprises four pin support members 3, out of which only three are visible in FIG. 1. The four pin support members 3 are arranged in the corners of a rectangular stereotactic frame 2 comprising four frame parts 11. Here, the frame parts 11 and the pin support members 3 are made of aluminium.

Figure 3A:
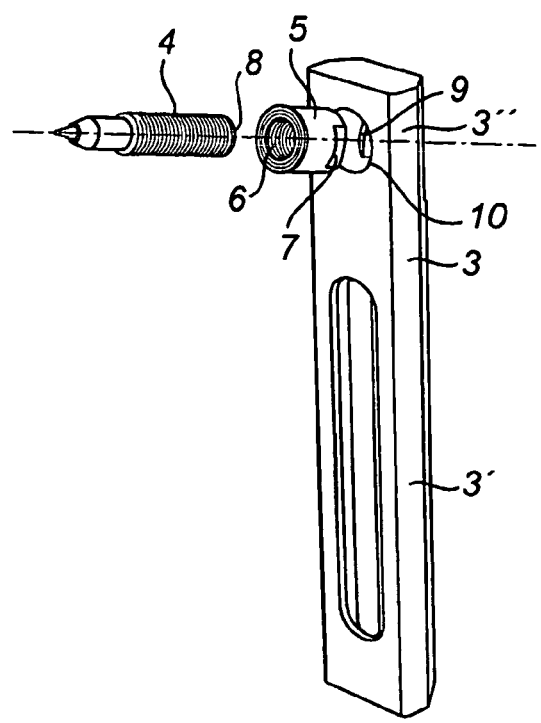
FIG. 3a is an exploded view of the fixation device of FIG. 1.
Figure 3B:
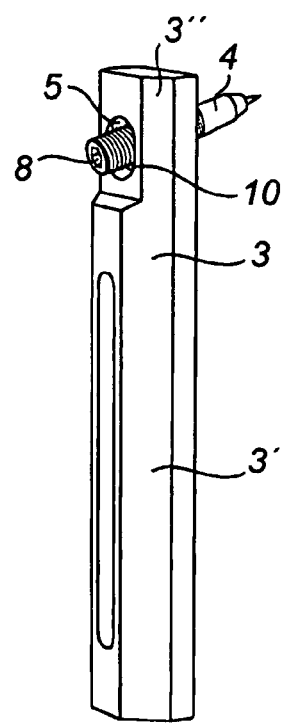
FIG. 3b is a first perspective view of the fixation device of FIG. 1.
Figure 3C:
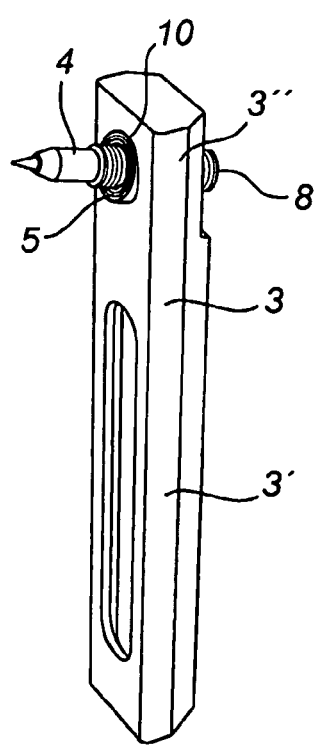
FIG. 3c is a second perspective view of the fixation device of FIG. 1.

In FIG. 3a, the fixation device 1 of FIG. 1 is shown in an exploded view. Each pin support member 3 supports a fixation pin 4. An insulation means 5 is arranged so as to restrict the electrical coupling between the pin support member 3 and the corresponding fixation pin 4.

The pin support member 3 comprises an elongate body having a frame attachment part 3' and a pin supporting part 3". The pin supporting part 3" comprises a receiving formation 10 for receiving the insulation means 5. The receiving formation 10 is in this embodiment in the shape of an unthreaded through bore, having smooth walls so as to receive the insulation means 5 by press fit. The receiving formation 10 is further provided with a surface structure 9, which in this embodiment cooperates with a surface structure 7 of the insulation means 5 to form a linear and rotational lock, which will be described in more detail below.

Figures 2A, 2B:
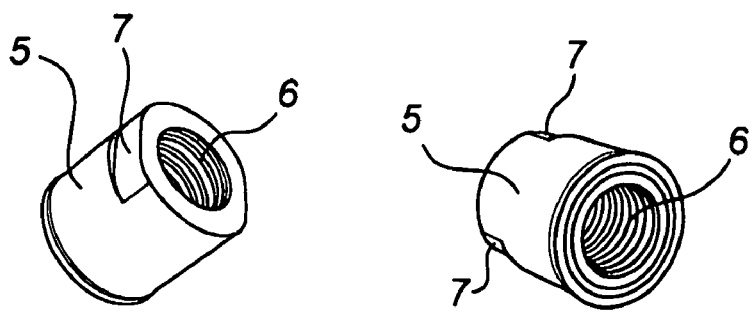
FIGS. 2a and 2b are a perspective views of an insulation means according to an embodiment of the invention.

FIGS. 2a and 2b are perspective views of an embodiment of an insulation means 5, which is used in connection with the fixation device 1 of FIGS. 1 and 3a to 3c. In this embodiment, the insulation means 5 is sleeve shaped for at least partly surrounding a fixation pin. The insulation means 5 is further provided with at least a section of internal threads 6 for cooperation with the external threads of a fixation pin 4, thus enabling adjustment of the position of the fixation pin 4 in relation to the insulation means 5. In this case, the entire inner surface of the through bore formed in the sleeve-shaped insulation means 5 is provided with inner threads 6.

Further, the outer surface of the insulation means 5 is unthreaded so as to be press-fit into a receiving formation 10 formed in the corresponding pin support member 3. The insulation means 5 is further provided with a surface structure 7 for forming a linear lock with a corresponding structure 9 of the receiving formation 10 of the pin support member 3. In this embodiment, the linear lock is achieved by an indentation formed in the insulation means 5 ending with an abutment surface extending in a direction crossing the introduction direction for introducing the insulation means 5 in a receiving formation 10 of the pin support member. A corresponding abutment surface extending in a direction crossing the introduction direction for introducing the insulation means 5 is formed in the receiving formation 10 by its surface structure 9.

Thus, when the insulation means 5 is introduced into the receiving formation 10 of the pin support member 3, the abutment surfaces of the surface structures of the insulation means 5 and the receiving formation 10, respectively, will eventually come into contact, thus inhibiting introduction of the insulation means 5 further into the receiving formation 10.

Also, the surface structures 9, 7 of the receiving formation 10 and the insulation means 5, respectively, form a rotational lock for the insulation means 5 in the receiving formation 10. This is advantageous in order to enable the fixation pin to be screwed to and from a fixation position without altering the position of the insulation means 5 in the pin support member 3.

In this embodiment, the rotational lock is accomplished by the surface structure 7 of the insulation means 5 and the corresponding surface structure 9 of the receiving section 10 each having an indentation or protrusion, respectively, locking against rotation of the insulation means 5 when set in the receiving section 10. The rotational lock effect is improved by the provision a plurality of surface structures, in this case of two surface structures 7 diametrically opposite each other on the insulation means 5 (See FIG. 2b), and two corresponding surface structures 9 diametrically opposite each other in the receiving formation 10.

Other variants of surface structures 7, 9 for realising the linear lock function or the rotational lock function may naturally be used. For example, with differently shaped surface structures 7, 9, snap lock mechanisms may be achieved, whereby the insulation means 5 may be snap-locked instead of press fit in the receiving formation 10. The size, number and distribution of surface structures 7, 9 may also be varied.

Figure 4:
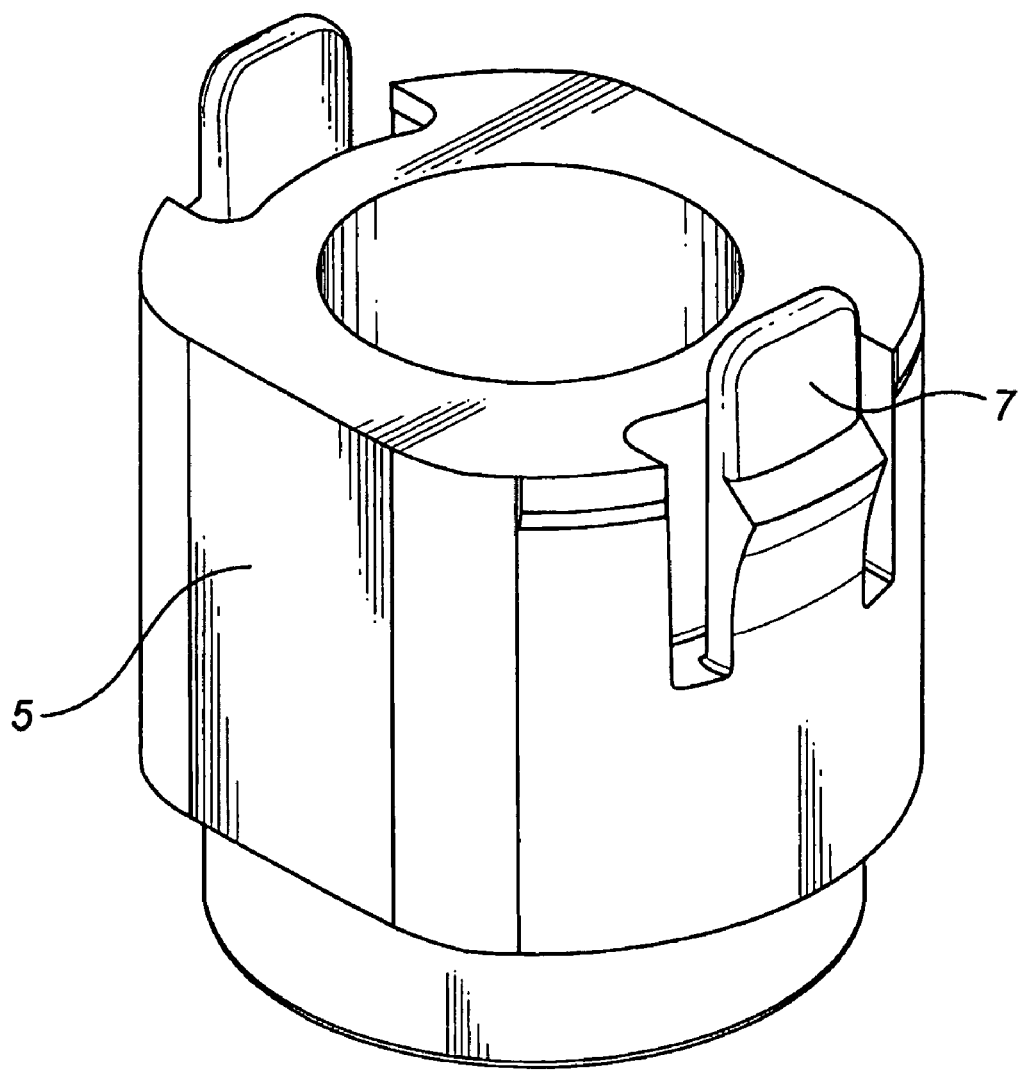
FIG. 4 is a perspective view of an insulation means according to a second embodiment of the invention.

FIG. 4 is a perspective view of a second exemplary embodiment of an insulation means 5. This insulation means 5 has a surface structures 7 in the form of flaps, which may form a snap-lock together with a corresponding structure in the receiving formation 10. Thus, a linear lock of the insulation means 5 in the receiving formation 10 is obtained. The insulation means 5 further has an outer shape having two flat surfaces, which may be used to obtain a rotational lock of the insulation means 5 in the receiving formation 10. Advantageously, the inner surface of the insulation means 5 may be provided with inner threads for co-operation with outer threads on a corresponding fixation pin.

For both embodiments of the insulation means described, as for other variants, the material of the insulation means 5 is preferably a non-conductive plastic. Such a plastic could have a resistivity greater than $10^{12}$ $\Omega$m, or even greater than $10^{15}$ $\Omega$m. Advantageously, the material should also withstand radiation sterilization. For example, glass fiber reinforced plastic may be used.

Returning to FIGS. 3a to 3c, it is seen how the fixation pin 4 extends through the insulation means 5, thus leaving an engagement means 8 at the distal end of the pin 4 exposed to be engaged when screwing said fixation pin to or from a fixation position. Thus, presently existing screwing tools for use with metal pins may be used for adjusting the fixation pin 4 without being hindered by the insulation means 5.

In this case, the engagement means 8 has the form of an internal polygonal structure, namely a hexagonal bore.

When assembling the fixation device of FIG. 3a for use during surgery, therapy or diagnostics, an insulation means 5 is initially introduced into the receiving formation 10 of the pin support member 3. The insulation means 5 is inserted into the receiving formation 10 until its surface structure 7 abuts the corresponding surface structure 9 of the receiving formation 10. Thereafter, a fixation pin 4 is threaded into the internal threads 6 of the through bore of the insulation means 5.

Alternatively, the fixation pin 4 may first be threaded into the insulation means 5, where after the insulation means 5 with the fixation pin 4 is introduced in the receiving formation 10 of the pin support member 3.

After use of the fixation device, the fixation pin is screwed out of the insulation means 5, and the insulation means 5 is removed from the pin support member 3.

Alternatively, the insulation means 5 is removed from the receiving formation 10 of the pin support member 3 together with the fixation pin 4, after which the fixation pin 4 is removed from the insulation means 5.

Advantageously, the fixation pin 4 and pin support member 3 are re-usable, and may be sterilised before use with another patient. The insulation means 5 may be disposable and thus discarded after one use only.

Other variants and embodiments of the invention may be envisaged within the scope of the invention. For example, the insulation means need not be sleeve-shaped, and may, instead of the through bore, be provided with a blind bore for attachment of the fixation pin. In order to facilitate press-fit of the insulation means in the receiving formation of the pin support member, the outer surface of the insulation means may be provided with wedge-shaped indentations. Also, the outer surface of the insulation means may be threaded for engagement with the receiving formation of the pin support member. The inside of the bore may be smooth for press-fit of the fixation pin therein, or it may be adapted for an other type of attachment of the fixation pin, such as for example snap-lock.

Also, the receiving formation of the pin support member may have different shapes so as to conveniently support the insulation means. It may also be convenient to form the pin support member and the insulation means as a unitary member, where both parts are sterilisable as one unit. Alternatively, the fixation pin and the insulation means may be provided together or as a unitary member.

Further, the pin support member need not, as in the accompanying drawings, necessarily be in the shape of a post 3. It is also feasible to arrange the insulation means 5 and the fixation pin 4 directly in a frame part 11, in which case said frame part 11 constitutes the pin support member.

It will be appreciated that the invention has been illustrated with reference to an exemplary embodiment and that the invention can be varied in many different ways within the scope of the appended claims.

Finally, it is to be noted that the inclusion in the appended claims of reference numerals used in the figures of drawings is purely for illustrative purposes and not to be construed as having a limiting effect on the scope of the claims.

The invention claimed is:

1. A device for fixation to a patient during neurological diagnosis, therapy or surgery, said device comprising:
    at least one fixation pin made of a non-magnetic, electrically conductive material for fixation to a patient;
    at least one pin support member that supports said fixation pin; and
    a single piece sleeve shaped insulator made of a non-conductive plastic material arranged to at least partially surround said fixation pin, said fixation pin extending through said sleeve shaped insulator,
    wherein said at least one pin support member includes a through bore formed therein for receiving said sleeve shaped insulator, said at least one pin support member having a surface structure formed within the through bore that cooperates with a corresponding surface structure formed on an outer surface of the sleeve shaped insulator, and wherein said cooperating surface structures provide a linear and rotational lock between the at least one pin support member and the sleeve shaped insulator.

2. The device according to claim 1, wherein said sleeve shaped insulator is made of a material having an electrical resistivity that is greater than an electrical resistivity of said pin support member and an electrical resistivity of said fixation pin, so as to restrict the electrical coupling between said pin support member and said fixation pin.

3. The device according to claim 1, wherein said sleeve shaped insulator is made of a material having an electrical resistivity greater than $10^5$ $\Omega$m.

4. A method for reducing heating in a fixation device for use during neurological diagnosis, therapy or surgery, said method comprising the steps of:
    providing said fixation device comprising at least one pin support member that supports a fixation pin;
    arranging a single piece sleeve-shaped insulator made of a non-conductive plastic material in said at least one pin support member;
    arranging the fixation pin to be supported in said sleeve shaped insulator so that a distal end of said fixation pin is accessible,
    wherein said at least one pin support member includes a through bore formed therein for receiving said sleeve shaped insulator, said at least one pin support member having a surface structure formed within the through bore that cooperates with a corresponding surface structure formed on an outer surface of the sleeve shaped insulator, and wherein said cooperating surface structures provide a linear and rotational lock between the at least one pin support member and the sleeve shaped insulator.

5. The method according to claim 4, wherein said sleeve shaped insulator is made of a material having an electrical resistivity that is greater than an electrical resistivity of said pin support member and an electrical resistivity of said fixation pin, so as to restrict the electrical coupling between said pin support member and said fixation pin.

6. The method according to claim 4, wherein said sleeve shaped insulator is made of a material having an electrical resistivity greater than $10^5$ $\Omega$m.

7. The method according to claim 4, wherein said sleeve shaped insulator is made of a non-conductive plastic material.

8. The device according to claim 1, wherein said at least one pin support member surface structure formed within the through bore that cooperates with a corresponding surface structure formed on an outer surface of the sleeve shaped insulator is a non-threaded surface structure.

9. The method according to claim 4, wherein said at least one pin support member surface structure formed within the through bore that cooperates with a corresponding surface structure formed on an outer surface of the sleeve shaped insulator is a non-threaded surface structure.

10. The device according to claim 1, wherein the corresponding surface structure formed on an outer surface of the sleeve shaped insulator is a non-threaded surface.

11. The method according to claim 4, wherein the corresponding surface structure formed on an outer surface of the sleeve shaped insulator is a non-threaded surface.

12. The device according to claim 1, wherein the sleeve shaped insulator has a threaded inner bore adapted to directly contact and hold the fixation pin in the insulator.

13. The method according to claim 4, wherein the sleeve shaped insulator has a threaded inner bore adapted to directly contact and hold the fixation pin in the insulator.

14. The device according to claim 1, wherein an entirety of the sleeve shaped insulator is made of the same non-conductive plastic material.

15. The method according to claim 4, wherein an entirety of the sleeve shaped insulator is made of the same non-conductive plastic material.

* * * * *